US012667263B2

(12) United States Patent
Pavlov et al.

(10) Patent No.: US 12,667,263 B2
(45) Date of Patent: Jun. 30, 2026

(54) METHOD OF MONITORING THE HYDRATION OF A LIVING BODY

(71) Applicant: SAMSUNG ELECTRONICS CO., LTD., Suwon-si (KR)

(72) Inventors: Konstantin Aleksandrovich Pavlov, Moscow (RU); Georgii Guramovich Megre, Moscow (RU); Alexey Viacheslavovich Perchik, Moscow (RU); Vladimir Germanovich Tsepulin, Moscow (RU); Daria Sergeevna Demidova, Moscow (RU); Egor Aleksandrovich Simchuk, Moscow (RU); Hyejung Seo, Suwon-si (KR); Jaehyuck Park, Suwon-si (KR); Minji Kim, Suwon-si (KR); Namseok Chang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 437 days.

(21) Appl. No.: 18/116,664

(22) Filed: Mar. 2, 2023

(65) Prior Publication Data

US 2023/0277067 A1      Sep. 7, 2023

Related U.S. Application Data

(63) Continuation of application No. PCT/KR2021/006454, filed on May 24, 2021.

(30) Foreign Application Priority Data

Oct. 30, 2020    (RU) ................................. 2020135857
Apr. 30, 2021    (KR) ........................ 10-2021-0056278

(51) Int. Cl.
*A61B 5/02* (2006.01)
*A61B 5/00* (2006.01)
*A61B 5/11* (2006.01)

(52) U.S. Cl.
CPC .................. *A61B 5/02* (2013.01); *A61B 5/11* (2013.01); *A61B 5/4866* (2013.01)

(58) Field of Classification Search
CPC ........... A61B 5/02; A61B 5/11; A61B 5/4866; G16H 20/60; G16H 40/67; G16H 50/20
See application file for complete search history.

(56) References Cited

U.S. PATENT DOCUMENTS

| | | |
|---|---|---|
| 10,206,619 B1 | 2/2019 | Lee et al. |
| 10,729,336 B1 | 8/2020 | Tran |

(Continued)

FOREIGN PATENT DOCUMENTS

| | | |
|---|---|---|
| CN | 1969743 A | 5/2007 |
| RU | 2013144060 A | 4/2015 |

(Continued)

OTHER PUBLICATIONS

International Search Report (PCT/ISA/210) issued from the International Searching Authority on Aug. 30, 2021 to International Publication No. PCT/KR2021/006454.

(Continued)

*Primary Examiner* — Jonathan T Kuo
(74) *Attorney, Agent, or Firm* — Sughrue Mion, PLLC

(57) ABSTRACT

A method for monitoring hydration of a living body of a user includes: obtaining an individual physiological data of the user; obtaining a sensor data associated with the living body of the user; determining, based on the sensor data, an estimated net amount of water intake of the living body and an estimated physical activity level of the living body; calculating daily water requirements for the living body (Continued)

MALE
AGE: 30 Y.O
WEIGHT: 75KG
ACTIVITY: MID

MINIMUM 2800 ml OF WATER PER DAY TO DRINK DRINK 250 ml OF WATER 400 ml OF LIQUID INTAKE 550 ml OF WATER LOST DRINK 450 ml OF WATER 1400 ml OF LIQUID INTAKE DRINK 200 ml OF WATER 3200 ml OF LIQUID INTAKE WELL DONE! TODAY OU RECEIVED HEALTH BENEFITS based on the individual physiological data and the estimated physical activity level; comparing the calculated daily water requirements for the living body with the estimated net amount of the water intake of the living body; and providing at least one individual recommendation based on a result of the comparing, the at least one individual recommendation being associated with a recommended amount of water for the user to take.

18 Claims, 8 Drawing Sheets

(56) References Cited

U.S. PATENT DOCUMENTS

| | | | | |
|---|---|---|---|---|
| 10,993,657 | B1 * | 5/2021 | Miller | G01N 25/62 |
| 2006/0231109 | A1 | 10/2006 | Howell et al. | |
| 2013/0338470 | A1 | 12/2013 | Ouwerkerk | |
| 2015/0196251 | A1 * | 7/2015 | Outwater | A61B 5/14551 |
| | | | | 600/324 |
| 2016/0003615 | A1 | 1/2016 | Biswas et al. | |
| 2016/0213315 | A1 | 7/2016 | Hyde et al. | |
| 2016/0220184 | A1 * | 8/2016 | Manion | A61B 5/4266 |
| 2016/0374588 | A1 | 12/2016 | Shariff et al. | |
| 2017/0103677 | A1 * | 4/2017 | Bhattacharjee | G16H 20/70 |
| 2017/0220772 | A1 | 8/2017 | Vleugels et al. | |
| 2019/0279758 | A1 * | 9/2019 | Marchal | G16H 20/60 |
| 2019/0333634 | A1 | 10/2019 | Vleugels et al. | |
| 2020/0000363 | A1 | 1/2020 | Miller et al. | |
| 2020/0305387 | A1 | 10/2020 | Gibbs | |
| 2020/0338118 | A1 * | 10/2020 | Parodi | A61B 5/4875 |

FOREIGN PATENT DOCUMENTS

| | | | |
|---|---|---|---|
| WO | 2015200904 | A1 | 12/2015 |
| WO | 2018044959 | A1 | 3/2018 |
| WO | 2019100086 | A2 | 5/2019 |

OTHER PUBLICATIONS

Written Opinion (PCT/ISA/237) issued from the International Searching Authority on Aug. 30, 2021 to International Publication No. PCT/KR2021/006454.

Russian Search Report issued from the Federal Service for Intellectual Property to RU Application No. 2020135857 on Oct. 30, 2020.

Russian Notice of Allowance issued from the Federal Service for Intellectual Property to RU Application No. 2020135857 on Oct. 30, 2020.

Communication issued Feb. 5, 2026 by the Korean Ministry of Intellectual Property in Korean Patent Application No. 10-2021-0056278.

* cited by examiner

METHOD OF MONITORING THE HYDRATION OF A LIVING BODY

CROSS-REFERENCE TO RELATED APPLICATIONS

This application is a by-pass continuation application of International Application No. PCT/KR2021/006454, filed on May 24, 2021, which based on and claims priority to Russian Patent Application No. 2020135857, filed on Oct. 30, 2020, in the Russian Patent Office, and Korean Patent Application No. 10-2021-0056278, filed on Apr. 30, 2021, in the Korean Intellectual Property Office, the disclosures of which are incorporated by reference herein in their entireties.

TECHNICAL FIELD

The present disclosure refers to methods and devices of human health monitoring and in particular to methods and devices that may be used to monitor the body state of a human and provides for optimal water intake.

BACKGROUND

Smartwatches have gained immense popularity among consumers. Smartwatch manufacturers are looking for new opportunities to provide useful features to consumers. While wearing the watch, a user may learn a lot of information useful for tracking his health (e.g., heart rate, pressure, body temperature, number of steps taken, concentration and type of air pollution around him). Smartwatches may also use basic functions, such as synchronization of notifications with a smartphone, an alarm clock, a calendar with event reminders, an Internet connection, financial payments.

During intense sports, fitness activities or other intense physical work, sweat loss may exceed the water intake. A deficit of water in the body can lead to dehydration, which can be accompanied by increased tiredness, loss of concentration, headaches. In extreme cases, severe dehydration of the body may lead to changes in the body's water-electrolyte balance, renal failure, heat stroke, or other life-threatening conditions.

Traditionally, in clinical and research practice, methods of isotope dilution using heavy water isotopes (D2O), testing of urine or saliva parameters and skin turgor observation may be used to estimate hydration. All of these methods are not possible to implement in mobile devices in a convenient to user way.

As described in US patent application pub. no. 2016/003615 A1 solution system tracks liquid consumption by a user from a liquid container using a flexible, network-connected, smart band. The smart band may detect orientations of the liquid container and identify swallows made by a user, basing on patterns of the detected orientations. The smart band may also estimate volume of liquid intake basing on characteristics of the detected swallows such as duration of a swallow. A detected swallow as well as swallow characteristics and the volume of liquid intake may be displayed on the smart band, and also may be transmitted to a server for storing and displaying on another network-enabled device. However, this technique involves significant user inconvenience, since to account for the whole amount of liquid intake, the user shall drink it only from a single container. Also, as drawbacks, it can be noted that this solution has a complex design and does not take into account the individual characteristics of the user, and, therefore, does not allow giving him recommendations by taking into account his physical activity and physiological characteristics.

Another device as described in U.S. Pat. No. 10,206,619 B1 provides hydration monitoring using electromagnetic radiation with a given intensity at several wavelengths of the optical range transmitted through a human body part. The output intensities and absorption coefficients of radiation by the human body are measured for each of these wavelengths. The slope of the absorption curve described by the Beer-Lambert law depends on the relative water content in the human body part where the measurement is made. This dependence allows the device to assess the level of hydration of the human body. The drawback of the proposed device is that it does not provide the user with individual recommendations (for example, in the event of dehydration) and does not monitor whether these recommendations have been followed.

Another method described in US patent application pub. no. 2016/374588 A1 is related to monitoring body hydration levels based on galvanic skin response measurements acquired by a wearable electronic device. One example provides a wearable electronic device including a sensor configured to measure galvanic skin response, a logic device, and a storage device including instructions executable by the logic device to operate a hydration monitoring mode, acquire a plurality of measures of galvanic skin response over time, present data regarding the plurality of measurements of galvanic skin response. The drawback of the proposed technique is that it does not provide the user with individual recommendations (for example, in the event of dehydration) and does not monitor whether these recommendations have been followed.

Another method as described in US patent application pub. no. 2020/000363 A1 describes an approach in which data is collected from various sensors, based on the data acquired, the user receives information regarding dehydration of the body. The sensor interface includes a first sensor operable to take a plurality of physiological measurements of a user over a period of time. The processing device may be coupled to the sensor interface. The processing device may be operable to receive the plurality of physiological measurements; determine a change in the plurality of physiological measurements; and determine a hydration condition measurement for a body based on the change of the plurality of physiological measurements. The device displays a hydration condition indicator of a user. However, this techniques does not provide the user with information regarding the volume of liquid intake, and the user does not receive individual recommendations regarding the required optimal amount of water intake.

None of these devices/methods make it possible to compare liquid intake and water loss by a user, and basing on such comparison, to provide the user with individual recommendations for water intake.

SUMMARY

The present disclosure provides a method and a device for monitoring hydration of a living body of a user.

A method for monitoring hydration of a living body of a user may include: obtaining an individual physiological data of the user; obtaining, from a plurality of physiological measuring sensors, a sensor data associated with the living body of the user; determining, based on the sensor data, an estimated net amount of water intake of the living body of the user and an estimated physical activity level of the living body of the user; calculating daily water requirements for the living body of the user based on the individual physiological data of the user and the estimated physical activity level of the living body of the user; comparing the calculated daily water requirements for the living body of the user with the estimated net amount of the water intake of the living body of the user; and providing, to the user, at least one individual recommendation based on a result of the comparing, the at least one individual recommendation being associated with a recommended amount of water for the user to take.

The determining the estimated net amount of the water intake of the living body of the user may include: estimating, based on the sensor data, an amount of water intake into the living body of the user and an amount of water loss from the living body of the user; and calculating the estimated net amount of the water intake of the living body of the user based on the amount of the water intake into the living body of the user and the amount of the water loss from the living body of the user.

The method may further include: receiving, from a user interface, a request for the at least one individual recommendation. The providing the at least one individual recommendation may be in response to the received request.

The amount of the water loss may include an amount of water loss due to sweating of the living body over a certain period of time.

The estimating the amount of the water loss may be additionally based on the estimated physical activity level.

The determining the estimated physical activity level may be based on an ambulatory step count.

The method may further include: providing a current state of water balance of the living body of the user associated with the amount of the water intake and the amount of the water loss.

The individual physiological data of the user may include at least one of age of the user, gender of the user, height of the user, or the weight of the user.

The method may further include: updating the at least one individual recommendation periodically over time.

The estimated physical activity level may include one of low activity, medium activity, or high activity.

The providing the at least one individual recommendation may include: when a water imbalance for the living body of the user, according to a the result of the comparing, is less than first threshold for a particular weight of the user, providing the at least one individual recommendation to the user after receiving from a user interface, a request for the at least one individual recommendation if the physical activity level includes low activity, and providing the at least one individual recommendation to the user before receiving the request if the physical activity level includes high activity.

The providing the at least one individual recommendation may further include: when the water imbalance for the living body of the user, according to a the result of the comparing, is both greater than or equal to the first threshold for the particular weight of the user and less than a second threshold for the particular weight of the user, providing the at least one individual recommendation to the user once if the physical activity level includes low activity, and providing the at least one individual recommendation to the user multiple times if the physical activity level includes high activity.

The providing the at least one individual recommendation may further include: when the water imbalance for the living body of the user, according to a the result of the comparing, is greater than or equal to the second threshold for the particular weight of the user, providing a warning about dehydration of the living body of the user to the user in addition to the at least one individual recommendation.

A device for monitoring hydration of a living body of a user may include: a plurality of physiological measuring sensors; and at least one processor disposed in electronic communication with the plurality of the sensors. The processor may be configured to: obtain an individual physiological data of the user; obtain, from the plurality of physiological measuring sensors, a sensor data associated with the living body of the user; determine, based on the sensor data, an estimated net amount of water intake of the living body of the user and an estimated physical activity level of the living body of the user; calculate daily water requirements for the living body of the user based on the individual physiological data of the user and the estimated physical activity level of the living body of the user; conduct a comparison to compare the calculated daily water requirements for the living body of the user with the estimated net amount of the water intake of the living body of the user; and provide, to the user, at least one individual recommendation based on a result of the comparison, the at least one individual recommendation being associated with a recommended amount of water for the user to take.

The processor being configured to determine the estimated net amount of the water intake of the living body of the user may include being configured to: estimate, based on the sensor data, an amount of water intake into the living body of the user and an amount of water loss from the living body of the user; and calculate the estimated net amount of the water intake of the living body of the user based on the amount of the water intake into the living body of the user and the amount of the water loss from the living body of the user.

The processor may be further configured to: receive, from a user interface, a request for the at least one individual recommendation. The processor may be configured to provide the at least one individual recommendation is configured to provide in response to the received request.

The amount of the water loss may include an amount of water loss due to sweating of the living body over a certain period of time.

The processor being configured to estimate the amount of the water loss may be configured to estimate additionally based on the estimated physical activity level.

The processor being configure to determine the estimated physical activity level may include determining based on an ambulatory step count.

The processor may be further configured to: provide a current state of water balance of the living body of the user associated with the amount of the water intake and the amount of the water loss.

The individual physiological data of the user may include at least one of age of the user, gender of the user, height of the user, or the weight of the user.

The processor may be further configured to: update the at least one individual recommendation periodically over time.

The estimated physical activity level may include one of low activity, medium activity, or high activity.

For providing the at least one individual recommendation the processor may be configured to: when a water imbalance for the living body of the user, according to a the result of the comparison, is less than first threshold for a particular weight of the user, provide the at least one individual recommendation to the user after receiving from a user interface, a request for the at least one individual recommendation if the physical activity level includes low activity, and provide the at least one individual recommendation to the user before receiving the request if the physical activity level includes high activity.

For providing the at least one individual recommendation the processor may be further configured to: when the water imbalance for the living body of the user, according to a the result of the comparison, is both greater than or equal to the first threshold for the particular weight of the user and less than a second threshold for the particular weight of the user, provide the at least one individual recommendation to the user once if the physical activity level includes low activity, and provide the at least one individual recommendation to the user multiple times if the physical activity level includes high activity.

For providing the at least one individual recommendation the processor may be further configured to: when the water imbalance for the living body of the user, according to a the result of the comparison, is greater than or equal to the second threshold for the particular weight of the user, provide a warning about dehydration of the living body of the user to the user in addition to the at least one individual recommendation.

Other technical features may be readily apparent to one skilled in the art from the following figures, descriptions, and claims.

Before undertaking the Mode for Invention below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system, or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF DRAWINGS

The above and other features and advantages of the present disclosure are illustrated in the following description, illustrated by the drawings, in which the following is presented.

DETAILED DESCRIPTION

Figure 1:
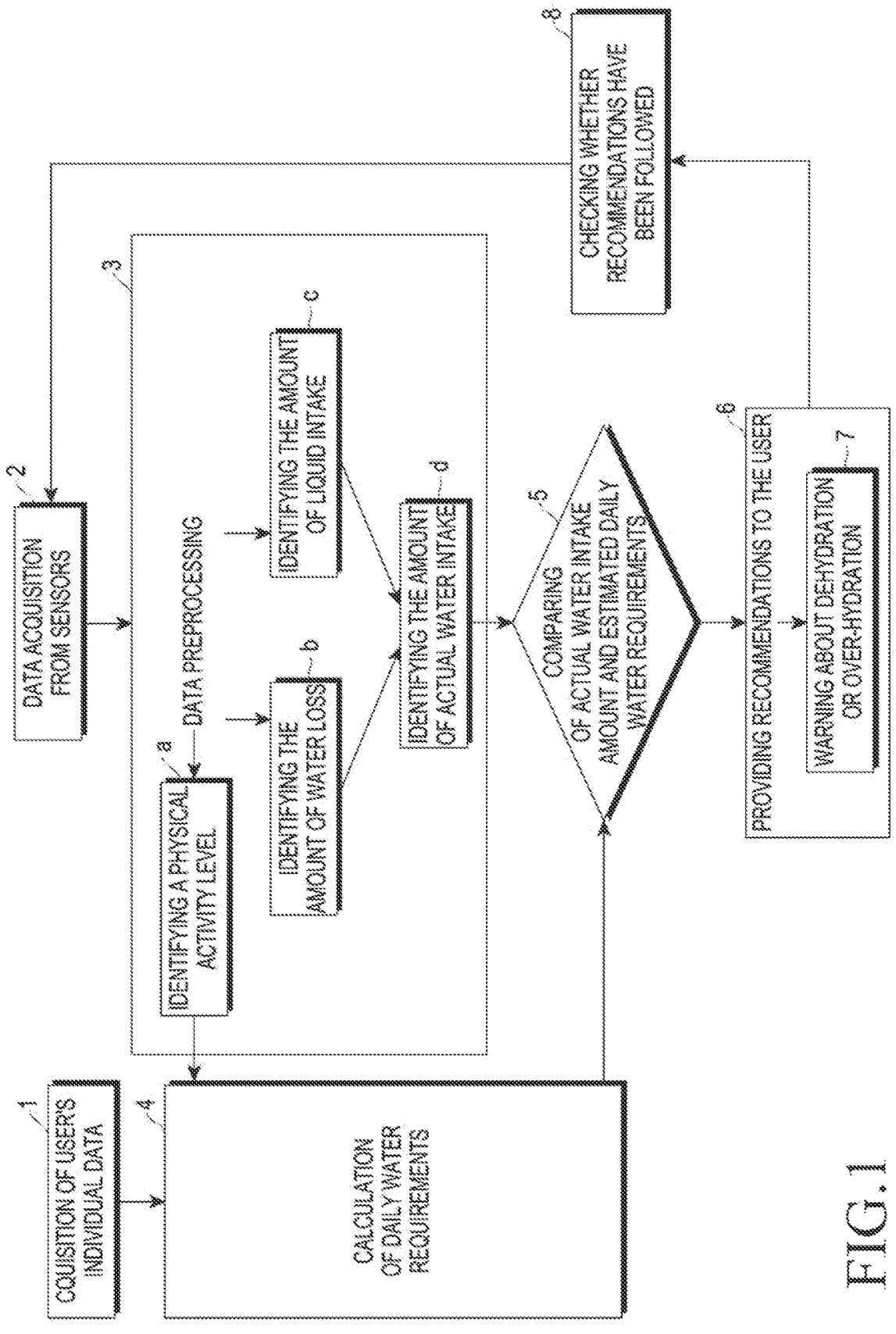
FIG. 1 illustrates a block diagram of a method and a device for monitoring the hydration of a human body according to an embodiment of present disclosure.

A method for hydration status assessment (saturation of the body with water) of a user is proposed. Accordingly, it is possible to provide individual recommendations to the user regarding the optimal water intake. It is also possible to warn the user (i) that the body is dehydrated or close to it, or (ii) about excessive liquid intake by the user. The proposed device provides high accuracy for users with any level of physical activity, and does not impose restrictions on the daily activities of the user. It is also possible to detect and calculate user's liquid intake gestures. This allows for automatic tracking of liquid entry into the body (events and estimation of liquid volume) by processing data from inertial sensors of a smartwatch. Additionally, this provides for an automatic estimation of water loss due to sweating during sports and daily life by processing data from inertial, optical and temperature sensors of the smartwatch. Monitoring the hydration balance of the user's body and individual recommendations to the user regarding the amount of water to be taken in accordance with the observed sweat loss and liquid intake may be provided. Thus, there is proposed a fully automatic device independent of the user (requiring no additional actions from the user) for hydration balance monitoring for the smartwatch, which provides the user with individual advices in a timely manner to prevent both dehydration and over-hydration of the body with water. Water over-hydration may be just as dangerous as dehydration. When the body is over-hydrated with water, the body temperature drops, there appears salivation, nausea, vomiting, impaired coordination of movements, cramps, muscle weakness, headache.

It should be noted that a person does not always drink just water, and also when eating food, not pure water enters the body, however, taking into account the error, it is possible to assume that the amount of liquid entering the body with food and drink is practically equal to the amount of water that has entered the body together with food and drink, the error from said assumption is small and is neglected in the disclosed embodiments. In other words, when calculating the water balance, the amount of body liquid intake is taken equal to the amount of body water intake.

The disclosed embodiments can be useful not only for users engaged in strenuous physical activity, but also for any other users, including those leading an inactive lifestyle.

The disclosed embodiments can be used in any suitable computing device of a user, comprising a processor and memory storing instructions for the processor to perform the steps of the proposed method. Such a device may be, but not limited to, a smartphone, a smartwatch, and other suitable devices, which will hereinafter be referred to as a smart band. The memory can be any medium for storing data, in particular a computer-readable storage medium.

The disclosed embodiments are based on the analysis of data from sensors used in a smart band. As it was mentioned above, the sensors can be inertial, optical and temperature, it is the presence of these sensors that is necessary and sufficient for implementation of the present disclosure. And also additionally/optionally, the following sensors can be used: body resistance sensor (bioimpedance sensor), which measures the impedance of the human body, galvanic skin response sensor; electrochemical sensors and other sensors directly or indirectly related to the body water balance. Additional sensors can serve for more accurate estimates of body hydration.

A machine learning algorithm may be used, which, basing on the data received from the sensors, may perform: estimation of water loss along with sweat, during physical exertion; and detection of user activity, such as nutrition, in particular liquid intake, by detecting individual gestures, and quantifying the amount of the user's liquid intake.

Basing on said estimation, the user may receive personalized recommendations for water intake in accordance with the needs of the user's body at the moment. Also, when forming recommendations, it is necessary to take into account the age, gender of the user, his weight and height.

In some embodiments, a function may be introduced into the smart band identifying the hydration balance of the user's body, which may include: automatic estimation of sweating, that is, the amount of water that has gone with sweating; automatic identification of liquid intake by the user with an estimate of the amount, that is, the user sees how many milliliters of water have been drunk; and providing a personalized recommendation to the user on the water intake in accordance with the user's physiological needs.

The system may be constantly trained and tested, that is, and the database to which the device may be connected is constantly updated, which may lead to providing more accurate recommendations to the user.

Operation of the algorithm requires a lot of data acquired from people with different individual parameters, in addition, the conditions in which test persons are located shall also differ from each other. That is, to acquire data in a variety of conditions, it is necessary to change the ambient temperature, humidity. For this purpose, during data acquisition, some test persons run on a treadmill, while different climatic conditions are artificially created by changing the temperature and humidity of the environment. Other test persons run down the street in various weather conditions. Also, the test persons can take liquid at a table while sitting or standing, table height and seat height can also be taken into account. In addition, different test persons can take liquid with the hand wearing the smart band or with the other hand without the smart band. All of the above are just examples of what can be considered when acquiring data to train the algorithm of the present disclosure.

During data acquisition, the following sensors may be used: accelerometer, gyroscope, heart rate sensor (plethysmograph) and temperature sensor. The duration of physical activity may be recorded for each test person. The signals received from the sensors may be preprocessed using a Gaussian and median filter to remove outliers that do not carry basic information. Basing on the data obtained from the signals, a set of features is calculated, which can be divided into statistical ones, being summarized information about a signal or a part of a value change signal over time, and frequency ones, being harmonic changes of all or part of a signal over a certain or entire period of time. The features that best correlate with water loss are identified and, therefore, when properly accounted for, allow estimating the liquid loss.

Further, according to the acquired data and calculated features, a regression model is trained (for example, "Boosting on trees"), the hyperparameters of which are at least the absolute error in cross-validation. After finding the hyperparameters, the regression model may be trained on all data.

The trained regression model, being implemented in a smart band, can provide individual characteristics to a user, basing on data that will be obtained from a specific user. To provide a personalized recommendation, the water loss is estimated using the trained regression model.

In some embodiments, the following sensors may be used: accelerometer, gyroscope, pulse sensor (plethysmograph), temperature sensor. To determine the characteristics of the user's individual water metabolism, in addition to the data obtained from these sensors, it is desirable to take into account the gender, age, height and weight of the user, the surface area of the skin (which may be calculated from the indicators of height and weight).

FIG. 1 illustrates a block diagram of a method and a device for monitoring the hydration of a human body according to an embodiment of present disclosure.

As it is shown in FIG. 1, the device for monitoring the hydration of a living body may include:

a user's individual data acquisition unit 1 (e.g., user interface) configured to receive input data including gender, age, weight, and height;

sensors (not shown in FIG. 1), which may include: an accelerometer, a gyroscope, a pulse sensor, and a temperature sensor;

a sensor data acquisition unit 2;

a data preprocessing unit 3, which may include: sub-unit (a) for identifying a physical activity level, sub-unit (b) for identifying the amount of water loss, sub-unit (c) for identifying the amount of liquid intake, and sub-unit (d) for identifying the actual amount of water intake;

a unit 4 for calculating daily water requirements;

a unit 5 for comparing the actual amount of water intake and the calculated daily water requirements;

a unit 6 for providing recommendations to a user.

The sensor data acquisition unit 2 may be connected to the data preprocessing unit 3.

In data preprocessing unit 3, the sub-unit (b) for identifying the amount of water loss and the sub-unit (c) for identifying the amount of liquid intake may be connected to the sub-unit (d) for identifying the actual amount of water intake.

In data preprocessing unit 3, the sub-unit (d) for identifying the actual amount of water intake may be connected to unit 5 for comparing the actual amount of water intake and the calculated daily water requirements, In data preprocessing unit 3, the sub-unit (a) for identifying a physical activity level may be connected to the unit 4 for calculating daily water requirements.

The individual data acquisition unit 1 may be connected to the unit 4 for calculating daily water requirements;

The unit 4 for calculating the daily water requirements may be connected to the unit 5 for comparing the actual amount of water intake and the calculated daily water requirements;

The unit 5 for comparing the actual amount of water intake and the calculated daily water requirements may be connected to the unit 6 for providing recommendations to a user.

The recommendations to the user may relate to the optimal water intake. If it is found that the body is on the verge of dehydration or the body is over-hydrated with water, then the recommendations to the user represent a warning 7 about dehydration of the user's body or over-hydration of the user's body with water.

The calculation of the daily water requirements may be based on: percentage (%) of body weight, skin surface area (ml/m$^2$), and sweat rate of body weight ml/kcal or ml/kg. Additional factors that may be taken into account are: age and gender, physical activity level, basal metabolic rate, and environmental factors.

The method for monitoring the hydration of a human body may be carried out as follows. A user puts on and activates a smart band, which may be a smartwatch, or any other suitable device attachable to the user's body. Hereinafter, for convenience, but not for limitation, such a device is called a "smart band". The smart band may include at least the following sensors: accelerometer, gyroscope, heart rate sensor (plethysmograph), temperature sensor. To take account of environmental conditions, the device may include sensors measuring, for example, ambient temperature, and humidity.

In order for the user to use the proposed function of the smart band, the user may enter his individual physiological identifying data regarding, for example, gender, age, height, weight, which are provided in the user's individual data acquisition unit 1, without this data the user will not be able to receive correct recommendations.

The smart band may start acquiring data using these sensors, the acquired data may be transmitted to the sensor data acquisition unit 2, wherefrom it is transmitted to the data preprocessing unit 3, where, basing on the readings of the sensors, the following values may be calculated using algorithms:

The amount of body water loss in the sub-unit (b) for identifying the amount of water loss. The trained machine learning regression model, as described above, predicts the amount of water lost from sweat over a period of time, for example, over a period of physical activity or over the entire day, this happens in sub-unit (b) for identifying the amount of water loss.

The amount of body liquid intake, this data is identified in sub-unit (c) for identifying the amount of liquid intake, the amount of body liquid intake being equal to the amount of body water intake.

The actual amount of body water intake, in sub-unit (d) for identifying the actual amount of water intake, basing on the amount of body liquid intake and the amount of body water intake.

The physical activity level identified in the sub-unit (a) for identifying a physical activity level. Basing on the data of inertial sensors (accelerometer and gyroscope), the level of a person's general physical activity is estimated, for example, by the number of steps per day, this is necessary to correct the user's daily water requirements, as a rule, the level of activity is divided into 3 classes: low, medium, high, and 700 ml is added to the daily rate if a particular person has an average level of activity and 1100 ml—if it is high. This data enter the sub-unit (a) for identifying a physical activity level.

Basing on the exploratory analysis, features were found that correlated with the estimate of water loss. To estimate the water loss, the correlated features are calculated and inputted in the trained regression model, which estimates the water loss in ml.

Basing on the data on the physical activity level and the user's individual data, the user's daily water requirements are calculated in the unit 4 for calculating the daily water requirements.

Further, the calculated data, namely the amount of body water loss and the amount of body liquid (that is, water) intake, may be recalculated into the actual data of the amount of the user's water intake. And then the actual amount of water intake and the calculated daily water requirements may be compared in the unit for comparing the actual amount of water intake and the calculated daily water requirements, the difference between the actual amount of body water intake and the calculated body daily water requirements is calculated.

Basing on the calculations made, a recommendation may be provided regarding the amount of water that the user should drink, for example, by the end of the current day. The recommendation can be updated continuously, and the recommendation can be provided when a certain level of lack of water in the body is reached or when the dehydration state is approaching.

If the amount of body liquid intake may be less than the critical threshold for water requirements, the user, together with information on the amount of water to be taken, receives a warning about the likelihood of dehydration (dehydration).

If the amount of body liquid intake is greater than the critical threshold for daily water requirements, the user, together with information on the amount of liquid, may receive a warning about excessive liquid intake.

After a recommendation on the amount of liquid is provided, the device may continue to acquire and calculate data, thus it turns out that the device monitors whether the recommendations have been followed. In the preferred implementation, the frequency of repeated notifications can be set by the user. The user can check the current state of the water balance at any time.

Thus, a comprehensive hydration monitoring of the body may be performed.

Obviously, there is a certain correlation between the received data and user behavior. Different users, depending on gender, age, weight and height, have certain levels of physical activity. To cluster users into groups, a regression model (for example, "Boosting in the trees") may be used, which breaks down the features for each subgroup of users (weight, height, age), thus giving values not only based on the sensors of the smart band, but also using the data about the user that he has entered. Basing on this, the features are selected that maximize the generalization of the model for all users.

Basing on the data from the accelerometer and gyroscope sensors, the drinking gesture can be distinguished from all other user gestures.

By detecting the time spent on the drinking gesture, it is possible to identify the amount of liquid that the user has drunk.

Below is an example of monitoring the hydration of a human body in detail.

The first factor for estimating the user's water balance may be estimation of the amount of water lost with sweat.

Basing on the signals received from accelerometer and gyroscope sensors, heart rate sensor, and temperature sensor, it is possible to identify the periods of user activity. For example, when the user starts to move, his speed, heart rate and temperature begin to increase.

The features are highlighted that can be divided into statistical ones, being summarized information about a signal or a part of a signal of changes in value over time, and frequency ones, being harmonic changes of all or part of a signal over some or all period of time. Once all the features have been compiled, the features may be identified that best correlate with water loss and, therefore, when properly accounted for, allow water loss to be estimated. When estimating water loss, features are calculated that correlate with the estimate of water loss and may be inputted in a regression model that estimates water loss.

The signals from the sensors enter the sensor data acquisition unit 2, then are processed in the data preprocessing unit 3, where the characteristic features that most affect the estimation of water loss are selected from the set of signals, namely the signals with characteristic features are transmitted to the sub-unit (b) for identifying the amount of water loss, which uses a machine learning regression model that estimates the amount of water loss. The characteristic features of the sensor signals are identified during the machine learning stage, so the trained regression model will select signals that have specific features during operation. Accelerometer signals provide information about the user's speed as well as the number of steps per minute. A plethysmogram gives information about the number of heart beats per minute. The temperature sensor provides information about body and ambient temperature. The data is filtered using a median filter and a Gaussian filter. Then the signals are normalized and the characteristic features related to the body water loss are selected.

There is a training sample and a test sample, which is split so that there are no gaps in the distribution of height, weight, sex and age. Next, all the features are calculated, then the features with the greatest correlation with each other are removed, since the correlation of random variables determines the linear change of one value when another random variable changes. If the features are strongly correlated with each other, then their contribution will be almost the same, therefore, all strongly correlated features can be dropped out except one, that is, features that are not correlated with each other fall into the regression model. Features are added iteratively to this number of features in the regression model, until the cross-validation error begins to increase. It is necessary to explain that during cross-validation, the sample is divided into N samples—training and validation—the algorithm is trained on the training sample and validated on the validation sample, after which the error is calculated on each of the validation samples, thus obtaining N estimates on different validation samples. Then the average error is taken over all N errors on the validation partitions. This experiment is repeated for different regression models, wherein different trained regression models differ only in different parameters, such as the number of trees and the maximum tree depth. After calculating cross-validation errors on different regression models with different parameters, the best model is selected by an error on cross-validation, after which a regression model is determined, the error of which is not only the smallest, but also is closest to the error on the test sample, and the test sample is formed from a large data set, about 25-30% of the entire data set is selected, which allows choosing the best model in terms of model parameters.

The algorithm produces a calculation of the estimate of water loss, normalized to the body surface area. Let $y$, $f \in \mathbb{R}$ be vectors of real water losses and estimated water losses, respectively, these vectors belong to the set of real numbers. Then, $$\bar{y} = \frac{1}{n}\sum_{i=1}^{n} y_i$$

is the average value of real water losses, $$\sigma_{tot} = \sum_{i}^{n} (y_i - \bar{y})^2$$

is the total quadratic sum, $$\sigma_{res} = \sum_{i}^{n} (y_i - f)^2$$

is the sum of square deviations, $$R^2 = 1 - \frac{\sigma_{res}}{\sigma_{tot}}$$

is the coefficient of determination (R2), which evaluates the quality of the water loss estimation algorithm.

Then the resulting value is multiplied by the body surface area and the calculated value of the amount of water loss with sweat is obtained.

To obtain a better accuracy in determining the parameters, the device for monitoring the hydration of a living body can be additionally equipped with a sensor, which, according to the optical characteristics of skin scattering, may provide information on the water content in the skin. Such a sensor can operate in both the visible and near infrared regions of the spectrum and acquires data on the water content in the user's subcutaneous layer.

Also, the proposed device can be additionally equipped with an impedance sensor for measuring the water content in the whole body. To do this, the first electrode may be located on the lower part of the smart band adjacent to the skin, the second electrode is isolated and placed on the body of the smart band. To measure impedance, the user may touch the second electrode with the hand not wearing the smart band.

Also, the proposed device can be equipped with a galvanic skin response sensor. Two electrodes of such a sensor can be located at the bottom of the smart band. This sensor measures the localized sweat production in a specific area. Basing on the data from this sensor, it is concluded how the pores of the whole body work.

Another sensor that can be additionally equipped with the proposed device is a chemical sensor containing microfluidic channels through which the user's sweat passes. The sensor may analyze the chemical composition of electrolytes in the user's sweat. By changing the ratio of electrolytes, a conclusion may be made about the hydration state of the whole body.

A user location detection sensor can optionally also be used. The user's location is identified by geolocation data (GPS), while, for example, the vehicle in which the user is located can be identified by speed and geolocation. In this case, via the Internet, data is requested about the weather at the user's location, since the body water loss depends, among other things, on weather conditions.

As an additional data source, a smart scale may transmit information to a smart band. A sensor for determining bioimpedance can be built into the smart balance.

An additional data source can also be various applications installed on a smartphone associated with a smart band.

And also an additional data source can be other wearable devices of the user, for example, headphones, which are connected to a smart band and/or a smartphone wirelessly. The headphones can incorporate temperature sensors, pulse sensors, microphones for identifying the process of drinking and food intake.

Also, an additional data source can be the smart home infrastructure to which the user's smart band is connected. It is possible to wirelessly connect the smart band to the fitness equipment the user trains on, and thus receive additional information from the exercise equipment.

Figure 2:
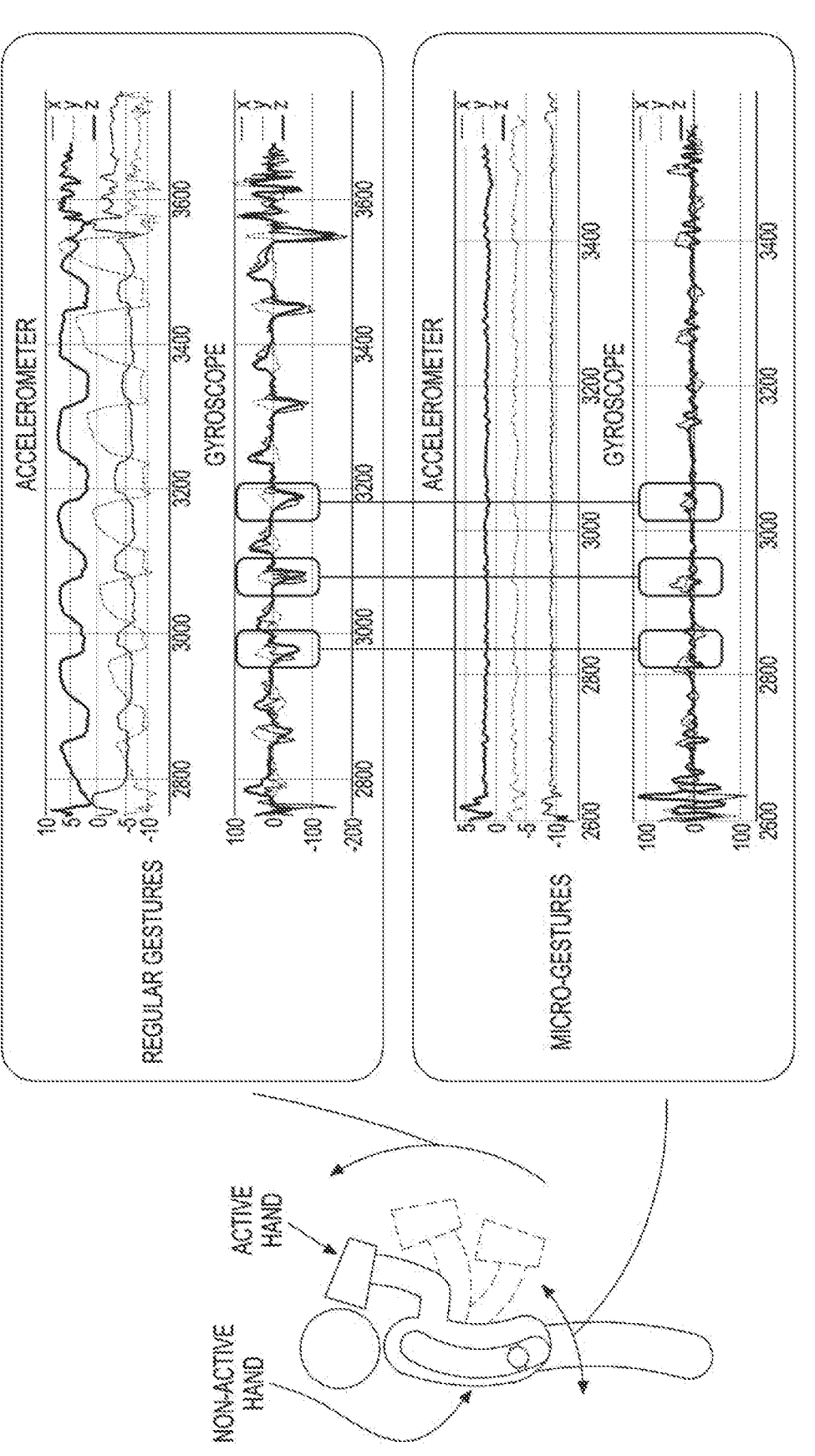
FIG. 2 illustrates estimation of liquid intake by a user according to an embodiment of present disclosure.

A second factor for assessing a user's water balance is the user's estimate of the user's liquid intake. FIG. 2 shows that such estimation can be made basing on the detection of a drinking gesture.

If the user makes a drinking gesture with the hand wearing the smart band, the gyroscope and accelerometer may record the movement signals of this hand. An example of signals recorded by these sensors during liquid intake is shown in FIG. 2. The upper two graphs show the signals recorded by the device worn on the active hand, and the two lower graphs—on the non-active hand. Each of the graphs shown contains three components corresponding to linear accelerations and angular velocities relative to the three coordinate axes of the sensors (x, y, z). The rectangular areas on the graphs mark the areas of the gyroscope signals corresponding to the drinking gesture and having its characteristic shape. Such repeating fragments of signals are observed both on a smart band worn on the hand, with which the user brings a container of liquid to his mouth, and on a second smart band located on a non-active hand.

Signals of hand movement to the mouth for drinking differ from signals of hand movement to the mouth for eating or doing exercises with raising the arms or other gestures. Each of these movements has its own specificity, for example, eating gestures are accompanied by pricking or scooping food, drinking gestures are characterized by their own turn of the hand and a longer holding of the hand at the mouth, etc., an algorithm trained on many examples can recognize various movements even if the user tries to imitate the drinking gesture with an empty hand, the algorithm recognizes that it was not a drinking gesture, and evaluates both the occurrence of the drinking gesture event itself and the duration of this gesture.

If the user makes a drinking gesture with a hand not wearing the smart band, the accelerometer and gyroscope record the micromovements of the non-active hand, corresponding to the movement of the whole body when making the drinking gesture with the active hand. In FIG. 2, the micromovements of the non-active hand and the movements of the active hand are marked with rectangles, time is plotted along the X-axes, the level of the accelerometer and gyroscope signals, respectively, along the Y-axes.

As an example, consider a gesture that a person performs during one swallow. Typically, this gesture begins with raising the hand with the vessel to the mouth. At the beginning of this gesture, a gyroscopic sensor records the acceleration of the hand. At the end of the movement, when the vessel with the liquid is at the person's mouth, inhibition is observed, which appears as a signal of a characteristic shape in the measurements taken from the gyroscope. The downward movement of the hand with the vessel also has characteristic features that allow detecting liquid intake gestures and estimate its volume.

The algorithms for detecting a liquid intake event and estimating its volume are based on a neural network model that simultaneously solves both the problem of detecting a liquid intake gesture and the problem of estimating the volume of this liquid. Accelerometer and gyroscope signals are pre-processed before being inputted in the specified model. Such processing may include digital filtering to remove noise, decimation, scaling, normalization, and the like.

Figure 3:
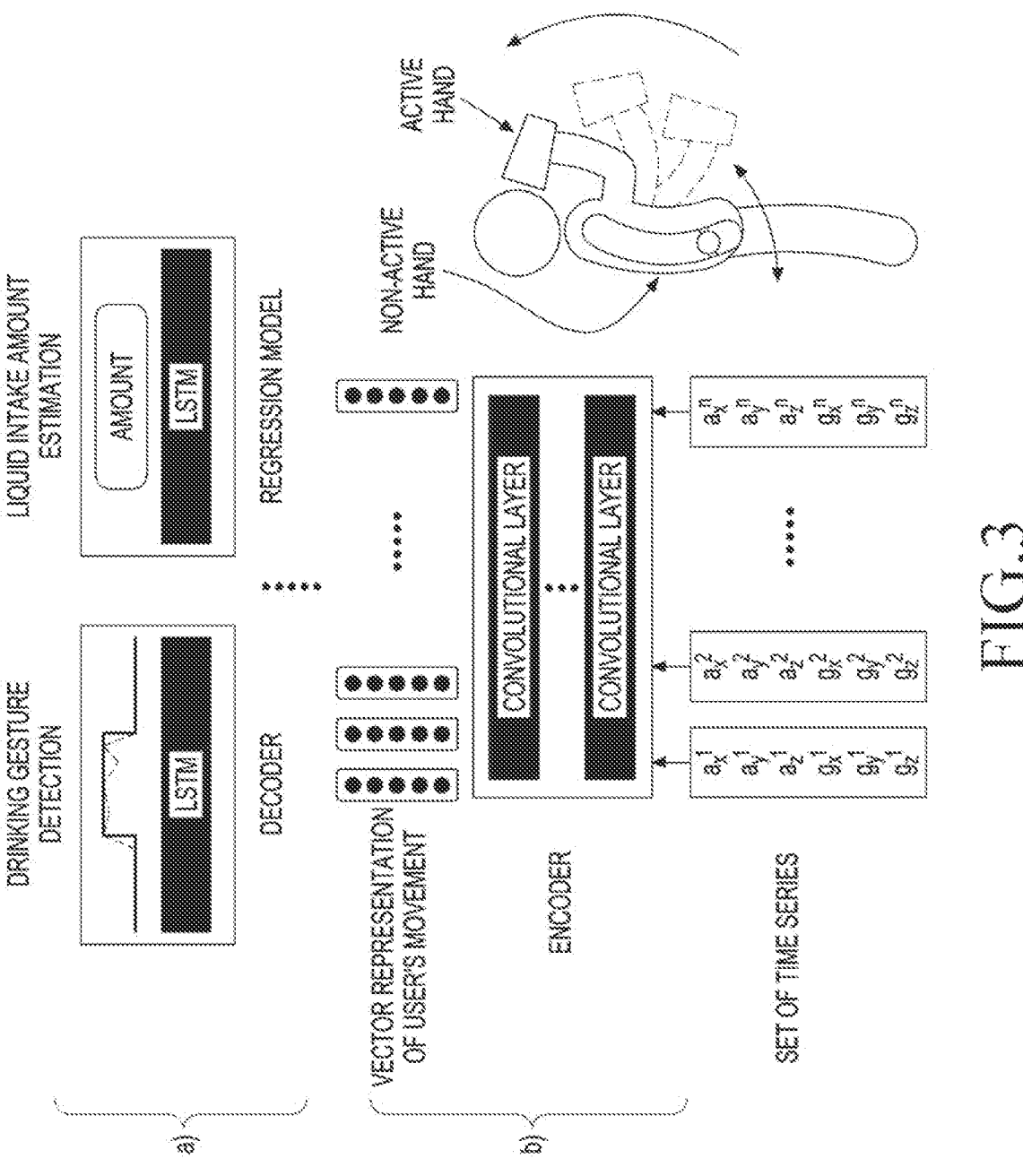
FIG. 3 illustrates a model for identifying a liquid intake gesture by a user according to an embodiment of present disclosure.

A schematic representation of the neural network model for identifying a drinking gesture is shown in FIG. 3.

The algorithm allows detecting a liquid intake gesture. Such a gesture is referred to as a movement during which a person swallows. A model in machine learning is understood as a functional transformation from input data to an estimated result, as well as a set of parameters required to implement this transformation.

During the operation of the proposed device, the accelerometer continuously measures the direction and magnitude of the acceleration vector, which comprises the acceleration of gravity, and the gyroscope measures the angular acceleration. The sequences of measurements from these sensors contain information about the trajectory of the device, and, therefore, the hand on which they are worn. This trajectory, in turn, describes the movements of the person.

In the sub-unit (c) for identifying the amount of liquid intake, the time sequences of signals from the accelerometer and the gyroscope are converted into a vector representation that describes what gestures the user makes at any time during the measurements. Next, a sequence of vector representations is analyzed.

The resulting sequence of vector representations can be considered as an input signal for the next functional level of the model. At the next functional level of the model, a decision is made, which of the gestures described by the corresponding vector representation refers to the event of fluid intake. Part (a), FIG. 3 is divided into two units. The left unit is responsible for detecting the gesture itself; at the output of this unit, data is received indicating the time at which the person made the drinking gesture. The right unit is used to estimate the volume of liquid that was drunk as a result of the gesture made. The volume of liquid drunk is estimated basing on the duration of the gesture, the angle of inclination of the vessel with the liquid.

Part (b) of FIG. 3 shows the calculation of the amount of user's liquid intake. A sequence of preprocessed measurements (the preprocessing operation is described above) is inputted in the neural network model, or rather its first layer. An encoder is a sequence of convolutional layers, each of these layers performs the operation of convolution of a set of input signals with a set of kernels belonging to the layer. The convolution operation comprises mixing of the input signals according to the ratios given by the weights that describe each of the specified kernels.

As a result of sequential application of the described operations for each of the encoder layers, a set of time series is formed at its output. The set of values of these time series for a particular moment in time is a numerical description of the movements that a person performed in a short period of time. This set of values is essentially a vector representation of such movements.

The set of time series, formed at the output of the encoder, is inputted into two units that solve the problem of detecting a liquid intake gesture during which a swallow is performed and estimating the volume of this swallow. In one of the embodiments, these units are built on the basis of recurrent layers (LSTM or GRU). In the course of the model operation, such layers store a state vector that characterizes the time sequence of the signals inputted in the signal layer. That is, this state vector describes a sequence of gestures that a person performed in a short time interval preceding the current gesture.

Figure 4:
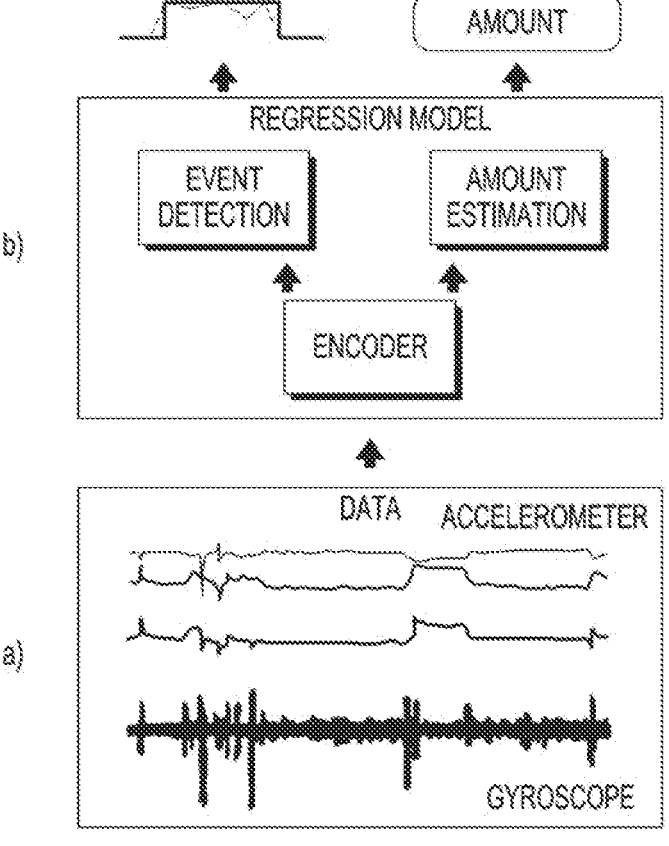
FIG. 4 illustrates training of the model for identifying the liquid intake gesture by the user according to an embodiment of present disclosure.

FIG. 4 illustrates training of the model for identifying the liquid intake gesture by the user according to an embodiment of present disclosure. Inputted in the model (b) is data (a) of the accelerometer and the gyroscope, which is a sequence of vectors containing 6 measurements for each moment in time: 3 numerals measured by the accelerometer, describing the vector of linear acceleration, and 3 numerals measured by the gyroscope, specifying the angular velocity. A sequence of sets of measurements is formed in such a way that the delay between two successive measurements is constant, if necessary, the interpolation of signals is performed to ensure this condition. Time is not explicitly transmitted to the model, while the time is encoded as a sequence of sensor measurements.

The main task of the proposed model is to continuously estimate the volume of liquid drunk by a person. This property of the model is provided as a result of training—the process of solving an optimization problem to find the parameters of the model, by which the weight coefficients are meant in the functions describing the transformation over the input variables. Upon completion of the learning process, the parameters are selected so that the minimum value of the error function calculated from the used dataset is achieved. An important feature of the learning process of the model proposed in the present disclosure is that while searching for the necessary parameters of the regression model, the solution of two problems is optimized, which consist in detecting a liquid intake gesture and estimating the volume of the liquid intake. In the process of searching for the parameters of this model from the training dataset, information is used not only about the volume of liquid, but also about the time intervals of gestures, as a result of which a person swallows. An error function is built, which contains two components, the first of which characterizes the quality of detection of gestures containing a swallow, and the second one characterizes the quality of the estimation of the volume drunk. During optimization, errors on both problems are taken into account. This approach greatly simplifies the learning process, thereby making it technically feasible.

The proposed approach to training allows finding such weights of the model, which ensure high quality of both the solution to the problem of classifying gestures into those related to drinking and others, as well as estimating the amount of liquid drunk as a result of one gesture.

A large number of datasets are used in the training process of the model, since each person makes a drinking gesture in a different way, and the vessels from which liquid can be taken can also vary greatly.

Figure 5:
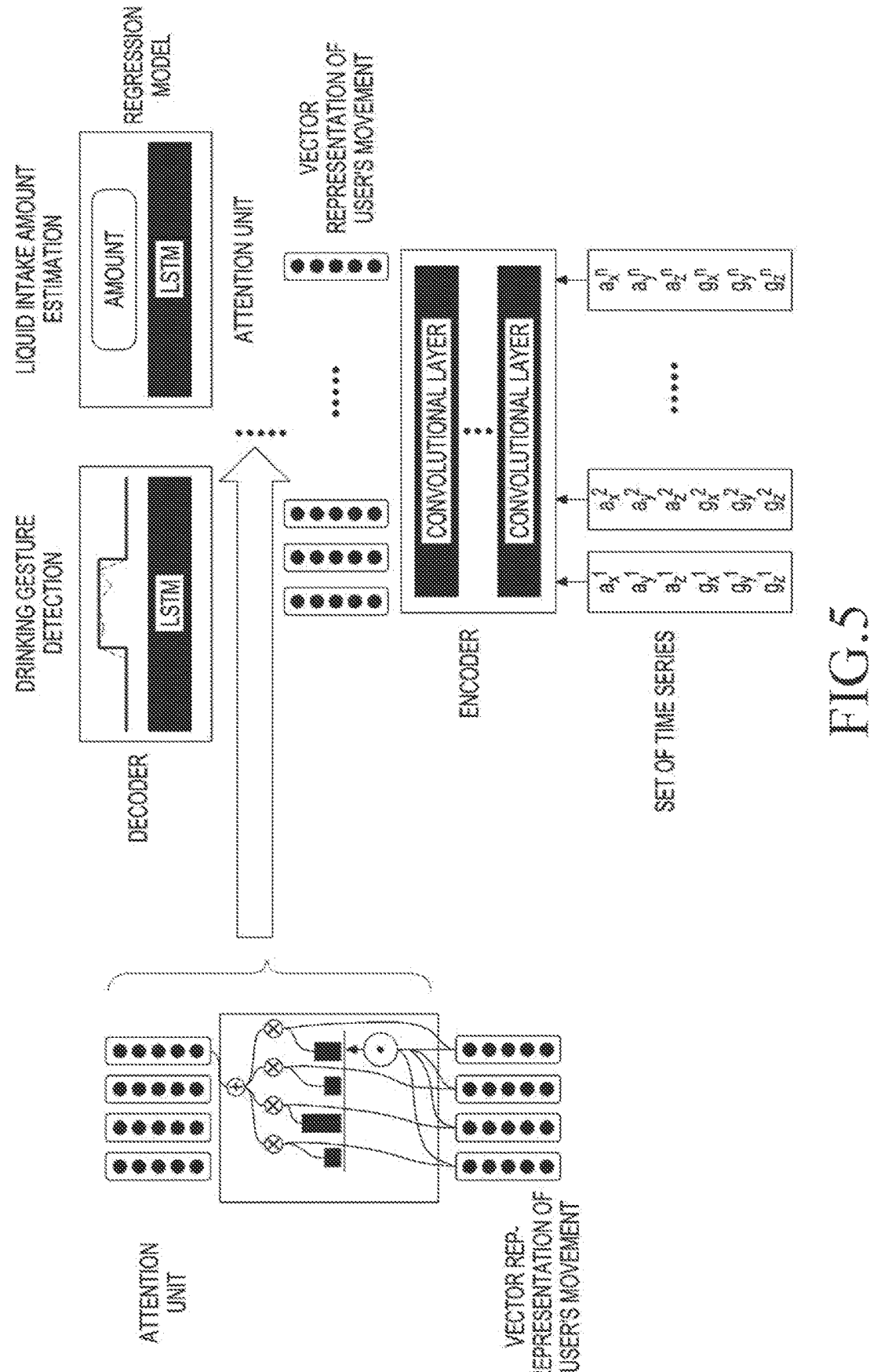
FIG. 5 illustrates the operation of the unit responsible for the ability of the model to use information only from specific gestures to predict the final result according to an embodiment of present disclosure.

The proposed model can be modified in several ways. One of the ways that will increase the accuracy of estimation is to supplement the model with a unit responsible for the ability to use information only from specific gestures to predict the final result, as it is shown in FIG. 5. In other words, thanks to the used unit, the model is capable of pay attention to specific features of signals in the entire temporal context. As it is shown in FIG. 5, when a segment of signal change at a certain time interval is at the input of a model with said unit, the model uses information from various points of said segment.

In other words, the accuracy of model estimation can be improved by adding an attention unit to it. The presence of this unit will allow the model to assign more weight to the vector representations of individual gestures, both associated with the swallow itself and auxiliary ones. Such gestures can contain information about the type and volume of the vessel used in the drinking process, which makes it possible to increase the accuracy of estimation of the volume of the drunk liquid. Also, studies show that the attention mechanism allows the model to store a longer temporal context (the history of the actions that the user performed). Obviously, this also has a positive effect on the quality of the model.

Figure 6:
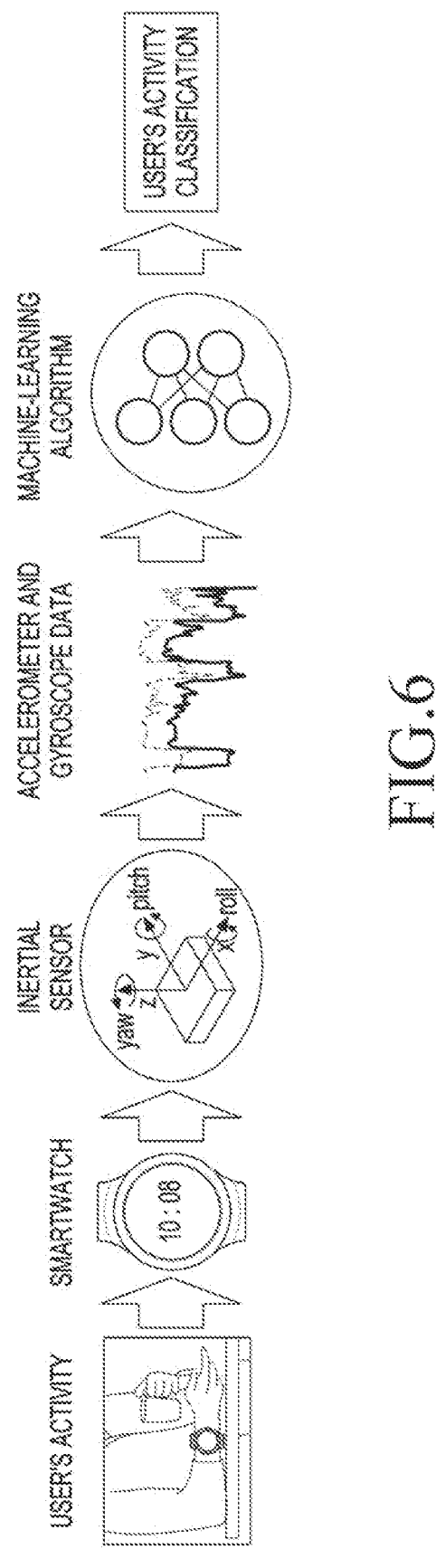
FIG. 6 schematically illustrates a general scheme for identifying any user's activity according to an embodiment of present disclosure.

By complementing the input signal processing algorithm, it is possible to define various other user gestures besides the drinking gesture (liquid intake). FIG. 6 schematically illustrates a general scheme for identifying any user activity according to an embodiment of present disclosure. That is, using an accelerometer and a gyroscope, as well as a regression model trained on a large number of examples with different features, it is possible to classify user actions based on the detection of motion patterns. Thus, it is possible to recognize various activities of the user, for example, but not limited to, an eating gesture, or, for example, it is possible to identify what kind of drink the user is taking—hot or cold, this is identified, for example, by the intake rate. Also, by modifying the model, it is possible to identify the moments of the user's life, when he is definitely not in the process of liquid intake. Also, the model can identify what the user is eating and the approximate liquid content of his food in order to take into account the amount of liquid taken with food in the total balance of the amount of the liquid intake. It is also possible to use the user's headphones, which are connected to the smart band wirelessly, microphones are built into the headphones, which capture sounds around the user while the user is wearing the headphones, in order to detect cases of drinking by analyzing sound patterns corresponding to, for example, swallowing liquid. That is, to detect liquid intake, it is possible to monitor the movement characteristics of the user and the sounds around the user. Certain movements, which the trained model recognizes as liquid intake, are recorded, and according to their duration in time, as well as by taking into account the individual parameters of the user, the amount of user's liquid intake is estimated. It should be noted that it is estimation of the amount of liquid that is made, and not an accurate calculation.

Additional data sources to improve the accuracy of estimating the amount of user's liquid intake can be data from other user devices, such as a smartphone, smartwatch, smart home infrastructure.

It is also possible to use an additional algorithm that identifies which hand is wearing the smart band, the dominant one, which a person uses more often, or not.

Figure 7A:
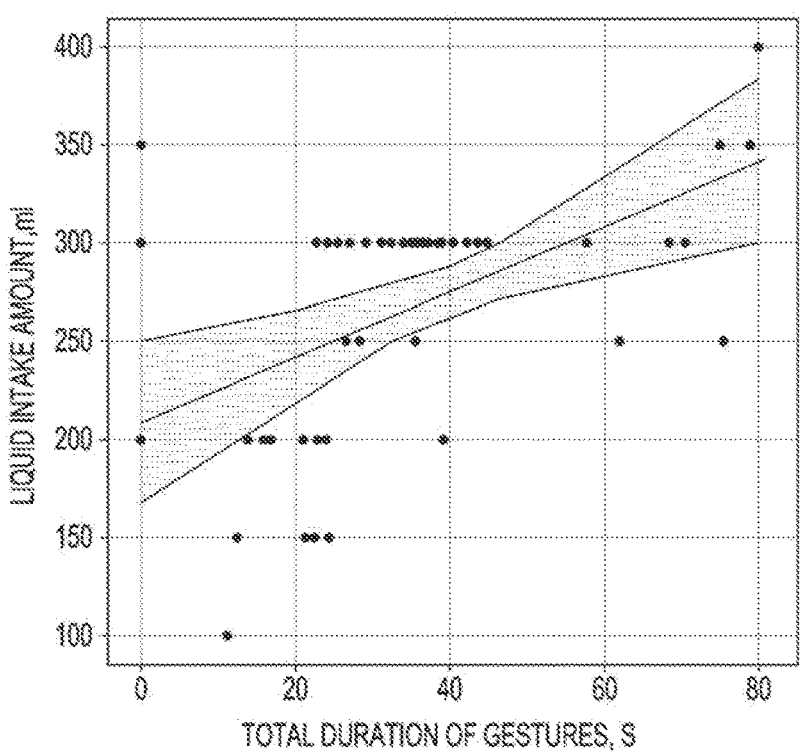
FIG. 7*a* illustrates the dependence of the amount of drunk liquid on the total duration of the gesture according to an embodiment of present disclosure.
Figure 7B:
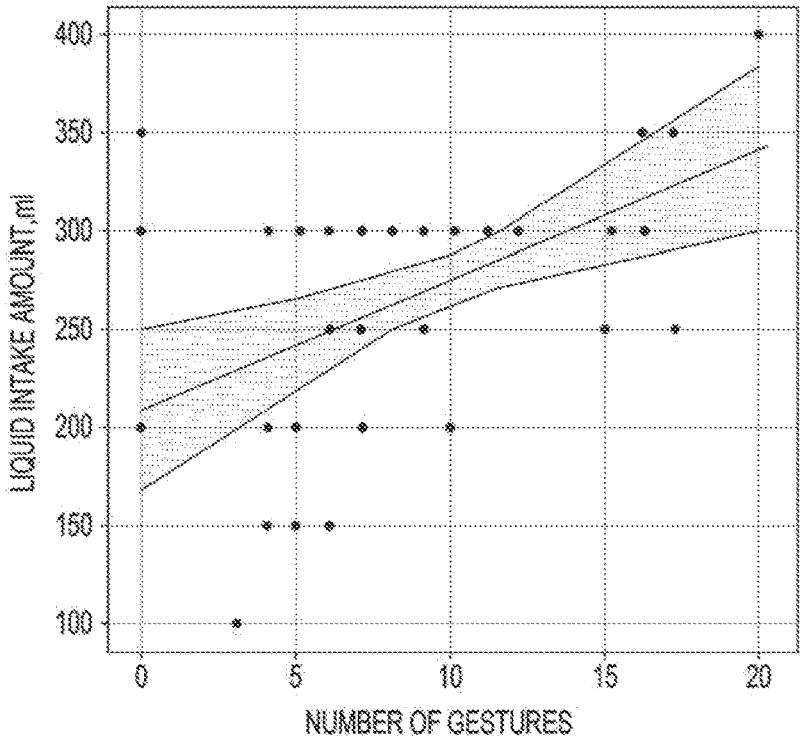
FIG. 7*b* illustrates the dependence of the amount of drunk liquid on the total number of gestures made according to an embodiment of present disclosure.

The following describes an illustrative example of estimating the amount of liquid drunk for one user. FIG. 7a illustrates the dependence of the amount of liquid drunk on the total duration of the gesture according to an embodiment of present disclosure. FIG. 7b illustrates the dependence of the amount of liquid drunk on the total number of gestures made according to an embodiment of present disclosure. That is, the volume of liquid drunk can be identified quite accurately even by these two dependencies, without using information about the shape of signals describing the trajectory of gestures. The example is for a simple algorithm with just two features. If we complicate the algorithm, for example, using additional features from the trajectory of the hand movement, it is obvious that a smaller error can be achieved.

When using only this information, it is possible to obtain a result with an error of the order of 10-15% for a specific user.

In the case of a negative hydration balance, that is, when the volume of user's liquid intake is less than the volume of water released by the user with sweat, there are three options for the development of events:

A) An insignificant imbalance of water in the body, that is, the water imbalance is less than 1% of the user's body weight. In case of low physical activity of the user, there is no need to notify the user. If the user is physically active, the user is notified of the current body water balance and recommendations for water intake.

B) A significant imbalance of water in the body, that is, the water imbalance is within 1%-2% of the user's body weight. In case of low physical activity of the user, the user receives a one-time notification about the current balance of water in the body. If the user is physically active, the user receives information about the current balance and a notification about the need to take water. With high physical activity, the smartwatch may turn on a counter, which reflects a decrease in the amount of water in the body.

C) Dangerous dehydration of the body, that is, when the water imbalance is more than 2% of the user's body weight. In case of low physical activity of the user, the user receives a notification with an urgent recommendation to take a certain amount of water. If the user is physically active, the user is notified of the required amount of water to drink, but here it should be borne in mind that a one-time large portion of water can be harmful.

Figure 8:
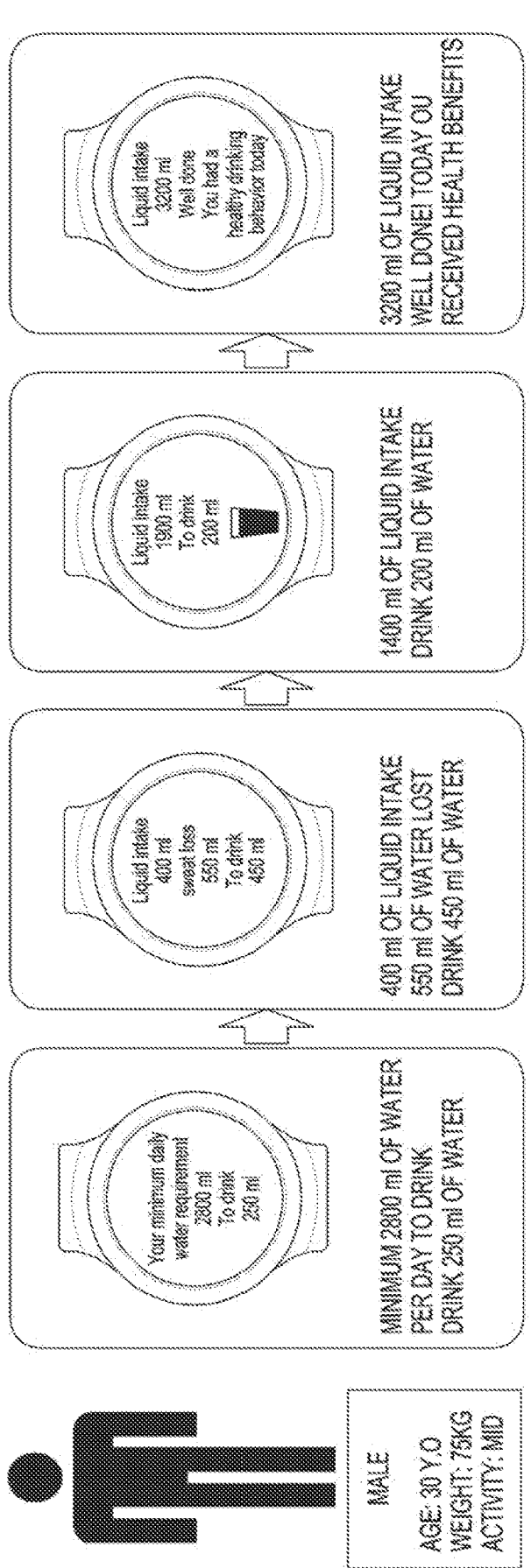
FIG. 8 illustrates an example of personalized recommendations that a user may receive throughout the day according to an embodiment of present disclosure.

FIG. 8 illustrates an example of personalized recommendations that a user may receive throughout the day according to an embodiment of present disclosure. For example, the user is a man, age 30, weight 75 kg, and the level of physical activity is medium. Height is an optional parameter, since the water demand of the body is usually estimated on the basis of weight with different coefficients for the age category and for the level of physical activity. The user's physical activity level is identified by the average number of steps per day and the average duration of increased physical activity per day (running, other sports/fitness).

In this example, when the user wakes up, the smart band provides a notification with a recommendation for the estimated daily need for water, in this case: "Minimum 2800 ml of water per day to drink. Drink 250 ml of water." After the user has exercised sports, the smart band, basing on the data on the volume of liquid intake, on the volume of water leaving with sweat, including after training, estimated during the day, provides a notification containing the following information: "400 ml of liquid intake. 550 ml of water lost. Drink 450 ml of water". During office work, basing on the data on the volume of liquid intake, on the volume of water leaving with sweat, estimated during the day, the smart band provides a notification: "1400 ml of liquid intake. Drink 200 ml of water." At the end of the day, the smart band may display the following notification: "3200 ml of liquid intake. Well done! Today you received health benefits!" All notifications are presented to the user on the screen of the smart band, depending on the data received.

A person without a smart band is guided only by a feeling of thirst, while a non-athletic person who decides to go jogging for the first time probably won't drink more water than he did before, since this is not part of his habits. If such a person drinks too little water, then there is a risk of dehydration, and he will feel symptoms such as dizziness, nausea and other problems with the gastrointestinal tract. If a person drinks too much water, then problems and health risks arise, in particular, if water does not have time to be consumed by the body, this is a great burden on the kidneys. If a person is a user of the proposed smartwatch, then already while running, he will be given information about the lack of water in the body, and in case of a risk of dehydration, a signal will be triggered in the smart band, drawing the user's attention to dehydration.

The embodiment is possible when estimation of water loss is not performed, but only estimation of the amount of liquid intake is performed. In this case, the user can also receive personalized recommendations for water intake, however, the water balance monitoring algorithm will work with low accuracy.

If the user has not inputted his individual data regarding gender, age, weight and height, in this case the system will still function. For example, the amount of sweat in this case can be estimated by the duration and intensity of physical activity. At the same time, the accuracy of estimating water losses will also be reduced.

It should be noted that, when hydration monitoring of the body, it makes no sense to take into account the excretion of water with urine. The kidneys maintain the internal balance of water in the body, if necessary, retain water or excrete excess water in urine. At the same time, being already in the bladder and when excreted from the body, urine does not in any way affect the hydration of body tissues. That is, the need for water and the elimination of urine from the body is a natural background process in a healthy person. While the present disclosure is intended to detect the following events: the user has been drinking very little for a long time; the user had high physical activity and a lot of water left with sweat (more than he has drunk); and the user drank too much water and his kidneys may not be able to cope with such a load.

In the events under consideration, it does not matter how often and in what quantity the urine is excreted from the body.

While the present disclosure has been described in connection with some illustrative embodiments, it should be understood that the essence of the present disclosure is not limited to these specific embodiments. On the contrary, the essence of the present disclosure is intended to include all alternatives, corrections, and equivalents that may be included within the spirit and scope of the claims.

In addition, the present disclosure retains all equivalents of the claimed invention even if the claims are changed in the course of consideration.

The invention claimed is:

1. A method for monitoring, by a device, hydration of a living body of a user, the method comprising:
   obtaining an individual physiological data of the user;
   measuring, via a plurality of physiological measuring sensors of the device, sensor data associated with the living body of the user;
   determining, based on the sensor data, an estimated net amount of water intake of the living body of the user and an estimated physical activity level of the living body of the user;
   calculating daily water requirements for the living body of the user based on the individual physiological data of the user and the estimated physical activity level of the living body of the user;
   comparing the calculated daily water requirements for the living body of the user with the estimated net amount of the water intake of the living body of the user; and
   providing, to the user, at least one individual recommendation based on a result of the comparing, the at least one individual recommendation being associated with a recommended amount of water for the user to take,
   wherein determining the estimated net amount of the water intake of the living body of the user comprises:
   estimating, based on the sensor data, an amount of water intake into the living body of the user and an amount of water loss from the living body of the user; and
   calculating the estimated net amount of the water intake of the living body of the user based on the amount of the water intake into the living body of the user and the amount of the water loss from the living body of the user,
   wherein the estimated physical activity level includes one of low activity, medium activity, or high activity, and
   wherein the providing the at least one individual recommendation comprises:
   when a water imbalance for the living body of the user, according to the result of the comparing, is less than first threshold for a particular weight of the user, providing the at least one individual recommendation to the user after receiving from a user interface, a request for the at least one individual recommendation if the physical activity level includes low activity, and providing the at least one individual recommendation to the user before receiving the request if the physical activity level includes high activity.

2. The method of claim 1, further comprising:
   providing a current state of water balance of the living body of the user associated with the amount of the water intake and the amount of the water loss.

3. The method of claim 2, wherein the estimating the amount of the water loss is additionally based on the estimated physical activity level.

4. The method of claim 1, further comprising:
   receiving, from a user interface, a request for the at least one individual recommendation,
   wherein the providing the at least one individual recommendation is in response to the received request.

5. The method of claim 1, wherein the determining the estimated physical activity level is based on an ambulatory step count.

6. The method of claim 1, wherein the individual physiological data of the user includes at least one of age of the user, gender of the user, height of the user, or the weight of the user.

7. The method of claim 1, further comprising:
   updating the at least one individual recommendation periodically over time.

8. The method of claim 1, wherein the providing the at least one individual recommendation further comprises:
   when the water imbalance for the living body of the user, according to the result of the comparing, is both greater than or equal to the first threshold for the particular weight of the user and less than a second threshold for the particular weight of the user, providing the at least one individual recommendation to the user once if the physical activity level includes low activity, and providing the at least one individual recommendation to the user multiple times if the physical activity level includes high activity.

9. The method of claim 8, wherein the providing the at least one individual recommendation further comprises:
   when the water imbalance for the living body of the user, according to the result of the comparing, is greater than or equal to the second threshold for the particular weight of the user, providing a warning about dehydration of the living body of the user to the user in addition to the at least one individual recommendation.

10. A device for monitoring hydration of a living body of a user, the device comprising:
    a plurality of physiological measuring sensors configured to measure data associated with the living body of the user;
    memory storing instructions; and
    at least one processor operable coupled to the plurality of the sensors and the memory, wherein the instructions, when executed by the at least one processor, cause the device to:
    obtain an individual physiological data of the user;
    obtain, from the plurality of physiological measuring sensors, measured sensor data associated with the living body of the user;
    determine, based on the sensor data, an estimated net amount of water intake of the living body of the user and an estimated physical activity level of the living body of the user;
    calculate daily water requirements for the living body of the user based on the individual physiological data of the user and the estimated physical activity level of the living body of the user;
    conduct a comparison to compare the calculated daily water requirements for the living body of the user with the estimated net amount of the water intake of the living body of the user; and provide, to the user, at least one individual recommendation based on a result of the comparison, the at least one individual recommendation being associated with a recommended amount of water for the user, wherein to determine the estimated net amount of the water intake of the living body of the user, the instructions, when executed by the at least one processor, cause the device to:

estimate, based on the measured sensor data, an amount of water intake into the living body of the user and an amount of water loss from the living body of the user; and calculate the estimated net amount of the water intake of the living body of the user based on the amount of the water intake into the living body of the user and the amount of the water loss from the living body of the user, wherein the estimated physical activity level includes one of low activity, medium activity, or high activity, and wherein for providing the at least one individual recommendation, the instructions, when executed by the at least one processor, cause the device to:

when a water imbalance for the living body of the user, according to the result of the comparison, is less than first threshold for a particular weight of the user, provide the at least one individual recommendation to the user after receiving from a user interface, a request for the at least one individual recommendation if the physical activity level includes low activity, and provide the at least one individual recommendation to the user before receiving the request if the physical activity level includes high activity.

11. The device of claim 10, wherein the instructions, when executed by the at least one processor, cause the device further to:

provide a current state of water balance of the living body of the user associated with the amount of the water intake and the amount of the water loss.

12. The device of claim 10, wherein to estimate the amount of the water loss, the instructions, when executed by the at least one processor, cause the device to estimate additionally based on the estimated physical activity level.

13. The device of claim 10, wherein the instructions, when executed by the at least one processor, cause the device further to:

receive, from a user interface, a request for the at least one individual recommendation, wherein the processor being configured to provide the at least one individual recommendation is configured to provide in response to the received request.

14. The device of claim 10, wherein to determine the estimated physical activity level, the instructions, when executed by the at least one processor, cause the device to determine based on an ambulatory step count.

15. The device of claim 10, wherein the individual physiological data of the user includes at least one of age of the user, gender of the user, height of the user, or the weight of the user.

16. The device of claim 10, wherein the instructions, when executed by the at least one processor, cause the device further to:

update the at least one individual recommendation periodically over time.

17. The device of claim 10, wherein for providing the at least one individual recommendation, the instructions, when executed by the at least one processor, cause the device further to:

when the water imbalance for the living body of the user, according to the result of the comparison, is both greater than or equal to the first threshold for the particular weight of the user and less than a second threshold for the particular weight of the user, provide the at least one individual recommendation to the user once if the physical activity level includes low activity, and provide the at least one individual recommendation to the user multiple times if the physical activity level includes high activity.

18. The device of claim 17, wherein for providing the at least one individual recommendation the instructions, when executed by the at least one processor, cause the device further to:

when the water imbalance for the living body of the user, according to the result of the comparison, is greater than or equal to the second threshold for the particular weight of the user, provide a warning about dehydration of the living body of the user to the user in addition to the at least one individual recommendation.

* * * * *